United States Patent [19]

Miki et al.

[11] 4,288,441
[45] Sep. 8, 1981

[54] NICOTINOYL PANTETHEINE DERIVATIVES

[75] Inventors: Tosaku Miki; Akashi Eriguchi; Yasushi Abiko; Kinya Kameda, all of Tokyo, Japan

[73] Assignee: Daiichi Seiyaku Co., Ltd., Tokyo, Japan

[21] Appl. No.: 173,447

[22] Filed: Jul. 30, 1980

[51] Int. Cl.³ ............... C07D 401/14; A61K 31/455; C07D 401/12
[52] U.S. Cl. .................... 424/266; 546/256; 546/263; 546/315; 546/318
[58] Field of Search ............ 546/256, 263, 315, 318; 424/264, 266

[56] References Cited
FOREIGN PATENT DOCUMENTS
40-18109 8/1965 Japan .

OTHER PUBLICATIONS
Harthon et al., *Arzneim-Forsch./Drug Res.*, 29 (II), No. 12, (1979).

Primary Examiner—John M. Ford
Attorney, Agent, or Firm—Oblon, Fisher, Spivak, McClelland & Maier

[57] ABSTRACT

A compound of the formula:

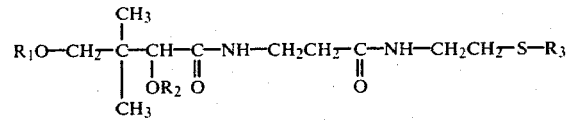

wherein $R_1$, $R_2$ and $R_3$ each represents a member selected from the group consisting of hydrogen and nicotinoyl, with the proviso that $R_1$, $R_2$ and $R_3$ do not all simultaneously represent hydrogen, and the nontoxic acid addition salts thereof.

6 Claims, 6 Drawing Figures

NICOTINOYL PANTETHEINE DERIVATIVES

BACKGROUND OF THE INVENTION

1. Field of the Invention

The present invention relates to nicotinoyl pantetheine derivatives and to therapeutically acceptable acid addition salts thereof, all of which have the effect of prolonging the duration of the free nicotinic acid level in the blood.

2. Description of the Prior Art

Many compounds are known which contain one or more nicotinoyl radicals. For example, pantothenol-nicotinate, which has the property of being able to decrease the blood cholesterol level, is disclosed in Japanese published patent specification No. 40-18109. Pentaerythritoltetranicotinate and meso-inositolhex-anicotinate are described in Arzneim.-Forsch./Drug Res., 859, volume 29(II), No. 12 (1979) by L. Harthon et al. A need continues to exist, however, for compounds which contain the nicotinoyl radical which exhibit improved activity for maintaining the level of free nicotinic acid in the blood.

SUMMARY OF THE INVENTION

Accordingly, one object of the present invention is to provide a compound containing at least one nicotinoyl radical which exhibits prolonged activity in maintaining nicotinic acid levels in the blood without any adverse effects.

Briefly, this object and other objects of the present invention as hereinafter will become more readily apparent can be attained by nicotinoyl pantetheine compounds of the formula:

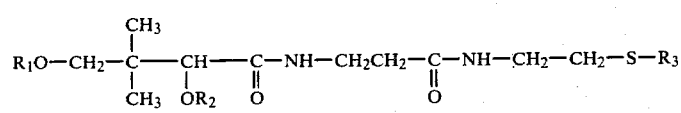

(I)

wherein $R_1$, $R_2$ and $R_3$ each represents a member selected from the group consisting of hydrogen and nicotinoyl, with the proviso that $R_1$, $R_2$ and $R_3$ can not all be hydrogen, and the nontoxic acid addition salts thereof.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
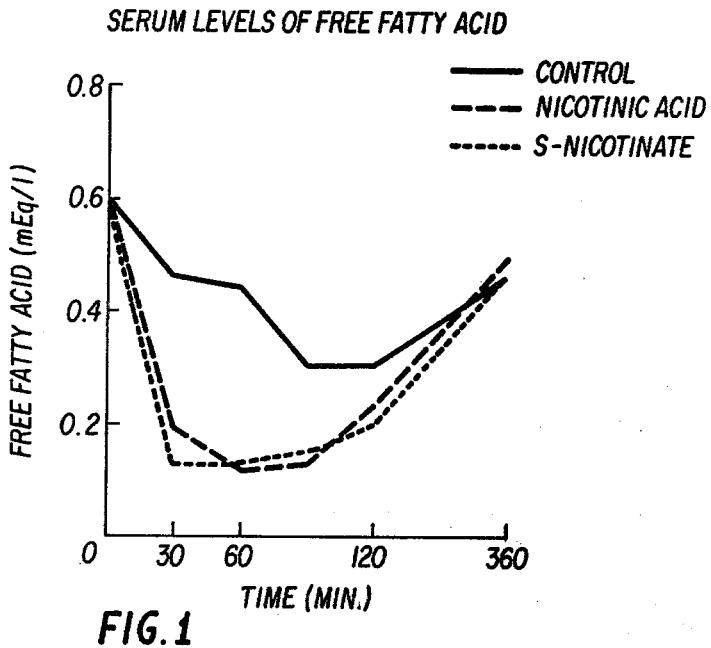
FIG. 1 is a graph showing serum levels of free fatty acid.
Figure 2:
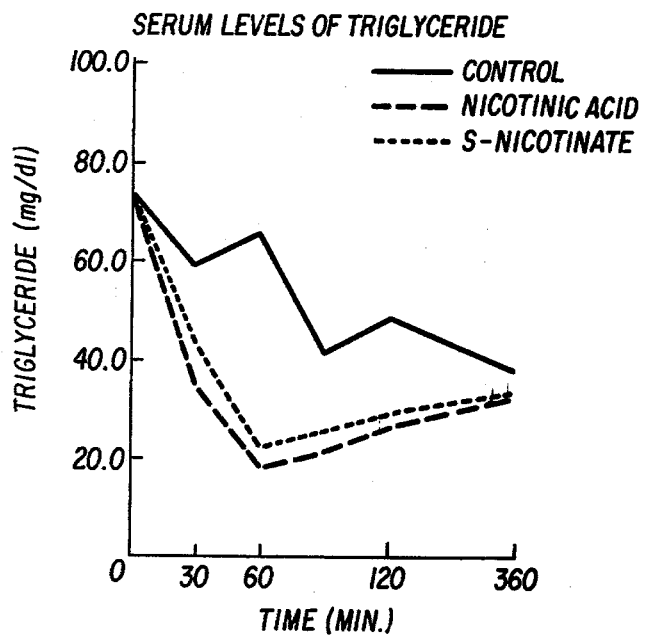
FIG. 2 is a graph showing serum levels of triglyceride.
Figure 3:
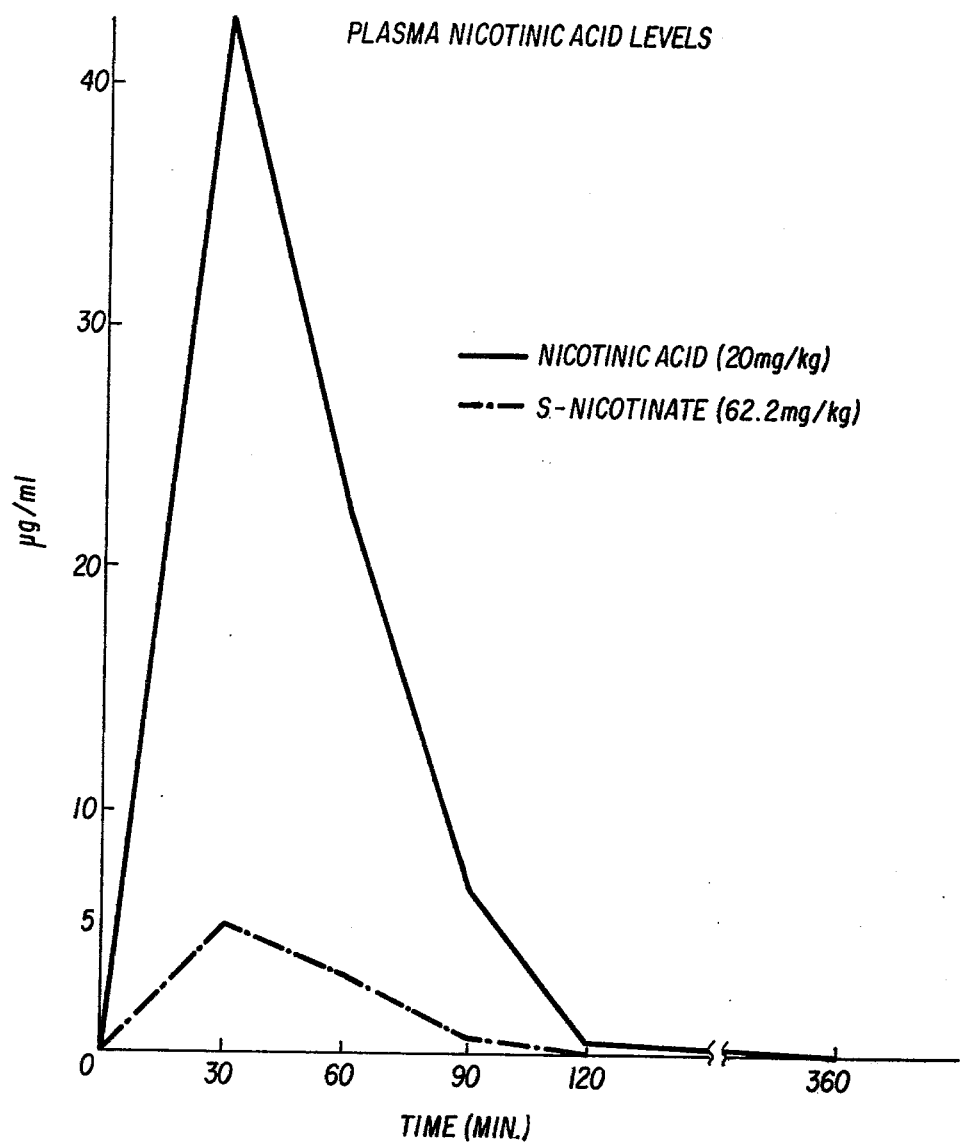
FIG. 3 is a graph showing plasma nicotinic acid levels.
Figure 4:
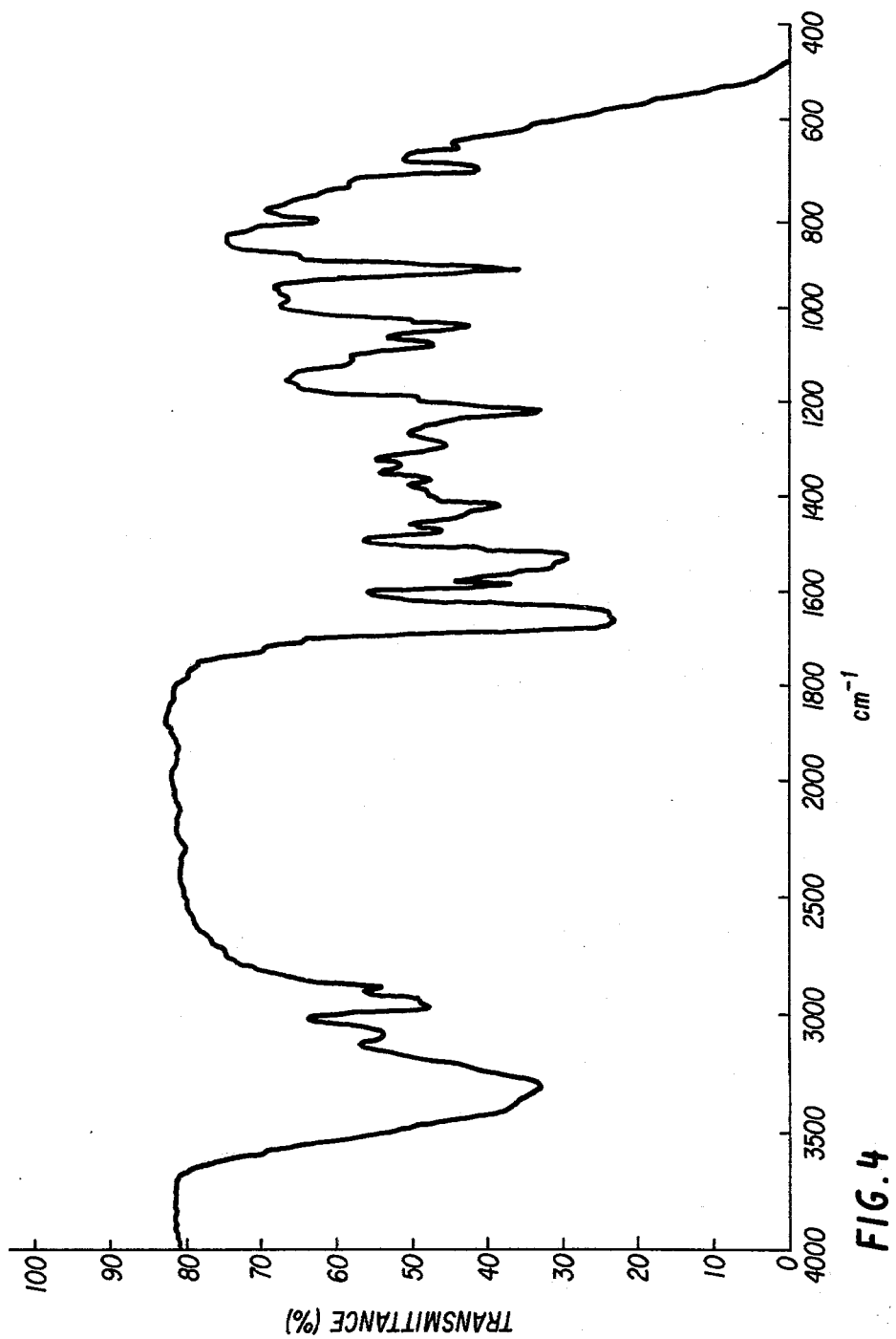
FIG. 4 is an infrared spectrum of 2,4-dihydroxy-N-[2-((2-mercaptoethyl) carbamoyl) ethyl]-3,3-dimethyl-butyramide S-nicotinate.
Figure 5:
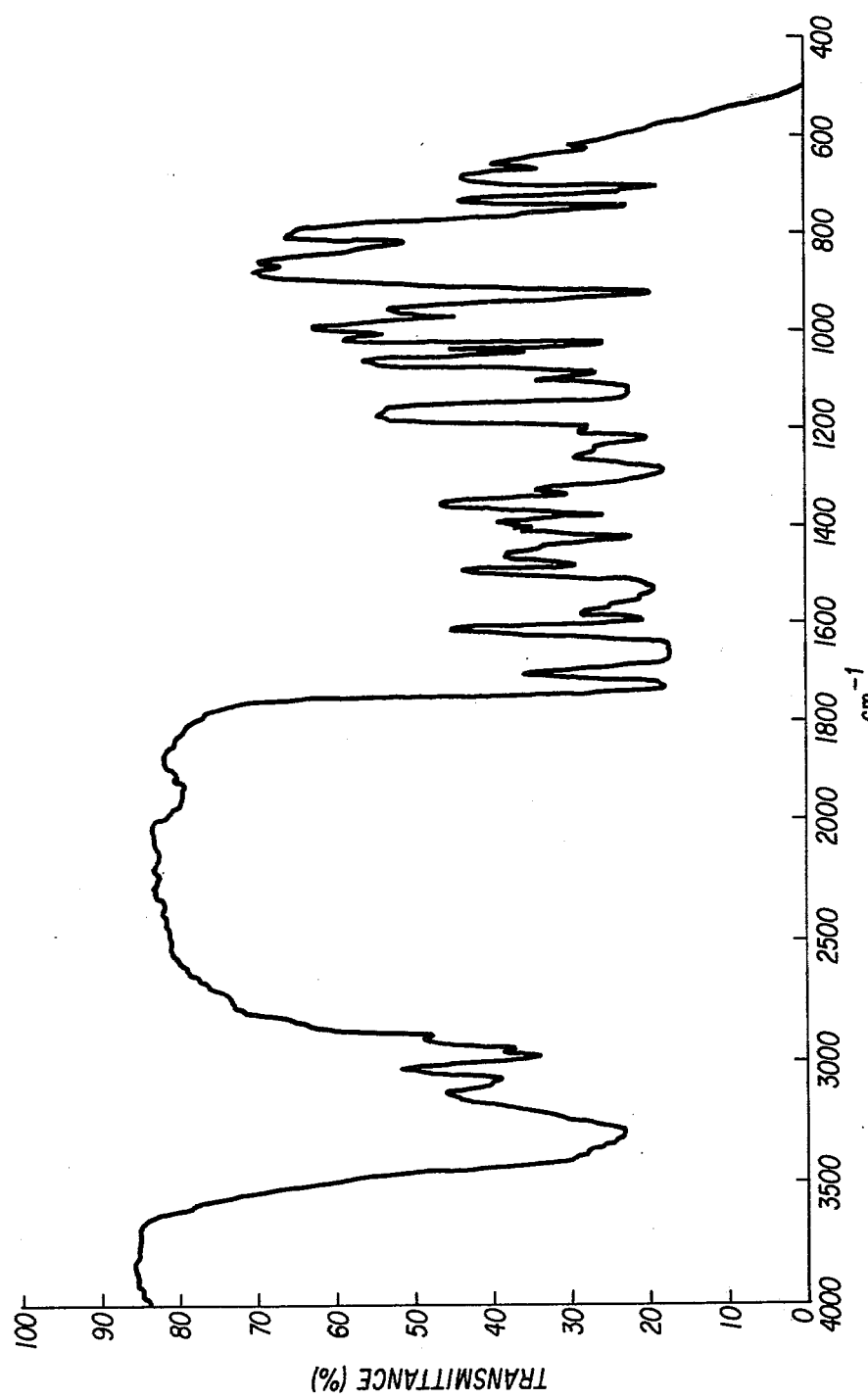
FIG. 5 is an infrared spectrum of 2,4-dihydroxy-N-[2-((2-mercaptoethyl) carbamoyl) ethyl]-3,3-dimethyl-butyramide-4,S-dinicotinate.
Figure 6:
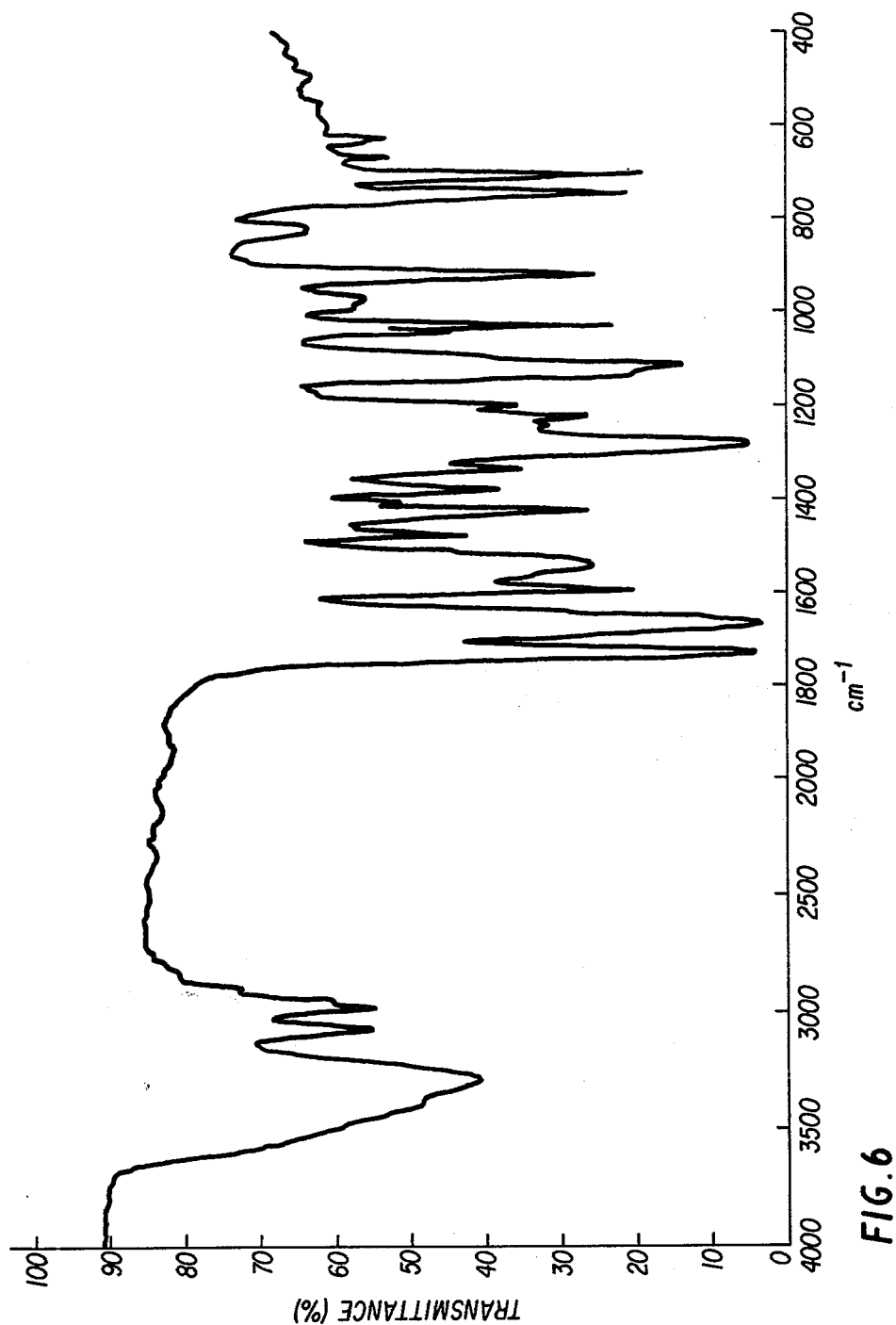
FIG. 6 is an infrared spectrum of 2,4-dihydroxy-N-[2-((2-mercaptoethyl) carbamoyl) ethyl]-3,3-dimethyl-butyramide-2,4,S-trinicotinate.

It is well known that nicotinic acid has a vasodilator effect and reduces the levels of lipids such as cholesterol, triglycerides, phospholipids and free fatty acids in blood. However, nicotinic acid has some adverse and undesirable effects when used in clinical treatment. For instance, the nicotinic acid level in the blood rapidly decreases when administered at normal dosage levels while, at higher doses, it causes various side-effects such as flushing of the face, itching and gastrointestinal impediments. Some of the side effects are caused by the rebound phenomenon which is, that after administration of nicotinic acid, the blood nicotinic acid level rapidly reaches a maximum level and then decreases in a short time.

In order to overcome these problems of maintaining an effective dosage level of nicotinic acid in the blood, several methods for the administration of nicotinic acid have been studied. One of the methods is to administer nicotinic acid in the form of a sustained release preparation. Another method involves the administration of an ester of nicotinic acid as a percursory drug which, after absorption, is hydrolyzed to give free nicotinic acid.

The compound of the present invention functions by acting as a precursor of nicotinic acid for maintaining the desired level of free nicotinic acid in the blood for prolonged periods of time. Furthermore, because the present compound exhibits very superior effects in removing impediments to lipid metabolism, the present compound is useful in the treatment of the likes of hyperlipemia, arterios clerosis, diabetes, and alcoholic fatty liver.

A representative embodiment of the compound of the present invention is 2,4-dihydroxy-N-[2-((2-mercaptoethyl) carbamoyl) ethyl]-3,3-dimethylbutyramide S-nicotinate (hereafter referred to as S-nicotinate) which can be prepared by reacting pantetheine with nicotinic acid chloride. The reaction is conducted in water in the presence of an amount of an alkaline hydroxide sufficient to act as an acid acceptor agent at room temperature or less. Furthermore, the addition of boric acid to the reaction medium may facilitate the reaction insofar as a highly pure compound can be attained. The other embodiments of the present compound can also be produced according to the procedure described above.

Another preparative procedure can be employed in which, for instance, the reactants described above are mildly heated at a preferred temperature of 40°-50° C. in the presence of an organic tertiary amine as an acid acceptor agent. Suitable tertiary amines include the likes of pyridine. If desired, the reaction can be conducted in the presence of an organic solvent such as benezene, a halogenated hydrocarbon or an ether, none of which adversely effect the reaction.

The crude product obtained as described by the above techniques is purified by conventional methodology such as by chromatography. The present compound can be isolated in the form of an acid addition salt if desired. Moreover, the present compound may be produced in an optically active form by conventional methods.

The present compound prepared by one of the above described methods exhibits nicotinic acid activity as shown in Table I (see also FIGS. I and II). That is, a representative compound of the present invention, S-nicotinate, decreases serum levels of free fatty acid and triglyceride in rats as well as nicotinic acid does. Judging from experimental results obtained, it seems that not only S-nicotinate hydrolyzed in the body, but also S-nicotinate itself has the same activity as nicotinic acid itself in maintaining a satisfactroy level of free nicotinic acid in the blood.

TABLE I

Serum levels of Free fatty acid and Triglyceride in rats

| Parameter | (n=6)Drug | 0 (min) | 30 (min) | 60 (min) |
|---|---|---|---|---|
| FFA (mEq/l) | Control | 0.60±0.03 | 0.46±0.03 | 0.44±0.03 |
| | Nicotinic Acid | | 0.19±0.09* | 0.12±0.01* |
| | S-Nicotinate | | 0.13±0.01* | 0.13±0.01* |
| TG (mg/dl) | Control | 73.8±3.8 | 58.8±3.8 | 65.5±8.5 |
| | Nicotinic Acid | | 35.0±2.3* | 18.0±0.7* |
| | S-Nicotinate | | 43.7±5.7 | 22.2±1.1* |

| Parameter | (n=6)Drug | 90 (min) | 120 (min) | 360 (min) |
|---|---|---|---|---|
| FFA (mEq/l) | Control | 0.30±0.02 | 0.30±0.02 | 0.46±0.05 |
| | Nicotinic Acid | 0.13±0.02* | 0.23±0.07 | 0.49±0.04 |
| | s-Nicotinate | 0.15±0.03* | 0.20±0.04 | 0.46±0.05 |
| TG (mg/dl) | Contol | 41.0±4.8 | 48.0±6.3 | 37.3±3.4 |
| | Nicotinic Acid | 21.2±2.5* | 26.2±1.1* | 32.5±3.1 |
| | S-Nicotinate | 25.5±3.3* | 29.2±1.6* | 33.5±8.0 |

*Significant difference from control (p 0.05)
FFA Free fatty acid,
TG Triglyceride Nicotinic acid (20 mg/kg of body weight) and S-nicotinate (62.2 mg/kg of body weight) were each suspended in 0.5% CMC solution and were orally administered to groups of rats in a volume of 10 ml/kg of body weight (62.2 mg of S-nicotinate corresponds to 20 mg of nicotinic acid in an equimolar relationship).

At the time specified in Table I, the rats were killed by pentobarbital (30 mg/kg, i.p.) anesthesia and blood was withdrawn by the carotid. The serum separated from the blood samples was assayed for free fatty acid (according to a variation of the Elphic method) and triglyceride (according to the enzyme method).

On the other hand, upon oral administration of each compound, i.e., nicotinic acid and S-nicotinate to groups of rats, the plasma nicotinic acid levels in the rats were studied. The results are shown in Table II and FIG. III. In this experiment, male SLC-SD strain rats weighting 202–234 g were used and the plasma nicotinic acid levels were assayed by high speed liquid chromatography. The other experimental conditions were the same as those described above.

TABLE II

| | 30min | 60min | 90min | 120min | 360min |
|---|---|---|---|---|---|
| Nicotinic Acid | 42.8±1.2 | 22.2±1.6 | 6.7±1.6 | 0.4±0.3 | 0±0 |
| S-Nicotinate | 5.2±0.3 | 3.3±0.3 | 0.7±0.4 | 0±0 | 0±0 |
| | | | (µg/ml) | | |

Apparently from Table II and FIG. III, the plasma nicotinic acid levels obtained with S-nicotinate are lower than those obtained with nicotinic acid all the time, especially 30 minutes after oral administration. However, in both cases, at 120 minutes after oral administration, nicotinic acid essentially disappeared. The data clearly show that compared with S-nicotinate, nicotinic acid induces a far larger rebound effect in the plasma nicotinic acid level than does S-nicotinate.

Another experiment using 10 mg/kg of body weight of nicotinic acid was performed. The experiment shows that the plasma nicotinic acid level which was achieved with 10 mg/kg of nicotinic acid reached a maximum of 8.3 µg/ml 30 minutes after administration which is the same result obtained with the administration of 20 mg/kg of nicotinic acid. However, at 60 minutes, the level fell to almost a trace amount or was not detectable. In short, since lower doses of nicotinic acid result in lower maximum nicotinic acid levels and in faster disappearance of nicotinic acid from the blood, lower doses of nicotinic acid may be free from the side effects caused by the rebound phenomenon. However, the desired therapeutic effect will be weak and will last only a short time.

The duration of nicotinic acid levels obtained with the present compound is longer than that obtained with free nicotinic acid which realizes the same maximum values of plasma nicotinic acid levels.

The effects of S-nicotinate were confirmed by an experiment in which alcoholic fatty liver rats were used according to the method described by A. Hosein et al., *Biochemical Pharmacology*, 24, page 1859, 1975.

In this experiment, male Sprague-Dawly rats, age 6 weeks, were treated as follows. The rats received 10 ml of 40% ethanol solution per kg of body weight for 3 days (at 10:00 AM on the day of sacrifice and at 4:00 PM on the other days) by gastric intubation. S-nicotinate was suspended in 0.5 (v/v)% Tween 80 aqueous solution and administered for five days (at 9:00 AM) including the day of sacrifice. After sacrificing the rats (at 1:00 PM), the total cholesterol was measured according to the Bennie Zak method (*American Journal of Clinical Pathology*, 27, page 583, 1957) and free fatty acid was measured by the method described by K. Itaya et al., *Journal of Lipid Research*, 6, page 16, 1965.

The experimental results are shown in Table III.

TABLE III

| Group (n-6) | Dose (mg/kg/day) | Serum Chloesterol (mg/dl) | Serum Free Fatty Acids (µEq/l) |
|---|---|---|---|
| Control | 0 | 99.6±4.80 | 313±46.25 |
| S-nicotinate | (0.1mmole/kg/day) | 79.0±4.23 | 236±21.33 |

From the above results it is clear that the compounds of the present invention have a superior effect in decreasing the serum cholesterol level and the serum free fatty acids levels as well.

The acute toxicity ($LD_{50}$) of S-nicotinate is shown in Table IV.

TABLE IV

Acute toxicity of S-nicotinate in mice

| Route | Sex | $LD_{50}$ (mg/kg) |
|---|---|---|
| P.O. | male (n=10) | >10000 |
| | female (n=10) | >10000 |
| I.V. | | 1600 |

P.O. = oral administration
I.V. = intravenous administration

The acute toxicity test was conducted as follows. STD ddY strain mice, weight male 17.2–20.5 g, female 17.5–19.7 g, were used. The mice were fed on forage and water freely and kept at constant environmental conditions (temperature 23±1° C., relative humidity 55±5%, and 12 hours light) before the test. Samples of S-nicotinate water solutions (0.3 ml/10 g of body weight) were administered to each group (n=10) of mice in order to achieve levels of 5 g/kg and 10 g/kg, respectively. One week after administration, all the mice were confirmed to be alive without any derangement.

The compound of the present invention and the pharmacologically acceptable acid addition salts thereof improve lipid metabolism and they may be prepared in conventional forms such as capsules, tablets, powders or injectable solutions according to known preparative techniques with pharmaceutically acceptable excipients. Furthermore, the present compound can be administered effectively at a level of 200–2000 mg/day for human beings.

Having generally described this invention, a further understanding can be obtained by reference to certain specific examples which are provided herein for purposes of illustration only and are not intended to be limiting unless otherwise specified.

EXAMPLE I

A 5.70 g amount of pantetheine was dissolved in 50 ml of a mixed solution of 1 M boric acid and 1 M potassium chloride. The pH of the obtained pantetheine solution was adjusted to 9.0 by addition of 1 N—NaOH solution. Then, 10.95 g of nicotinic acid chloride hydrochloride was added to the solution gradually with continued stirring and cooling with ice for 3.5 hours. The reaction was maintained at pH 8.7–9.0 at all times by addition of appropriate amounts of 1 N—NaOH solution to the reaction system.

After the reaction, the reaction solution was adjusted to pH 6 by the addition of 5% hydrochloric acid and extracted with ethylacetate. The extract solution was washed with sodium bicarbonate solution and then with water. After drying the extracted solution, the solvent was evaporated. The obtained residue was applied to a silica gel chromatographic column containing 300 g of silica gel and elution was carried out with chloroform-methanol (15:1) to give 2.51 g of 2,4-dihydroxy-N-[2-((2-mercaptoethyl) carbamoyl) ethyl]-3,3-dimethylbutyramide S-nicotinate as a colorless oily product.

Elemental Analysis $C_{17}H_{25}N_3O_5S$: Calculated: C 53.25, H 6.57, N 10.96, S 8.36: Found: C 53.23, H 6.70, N 10.56, S 8.25.

IR spectra (Liquid-film method) ... FIG. IV
NMR spectra

| CD$_3$COCD$_3$ | | |
|---|---|---|
| | δ: | 0.90(3H, s), 0.96(3H, s) |
| | | 2.49 (2H, t, 6.7Hz) |
| | | 3.45 (8H, m) |
| | | 4.00 (1H, broad) |
| | | 4.40 (1H, broad) |
| | | 5.14 (1H, m) |
| | | 7.62 (1H, d, d, 8.1Hz, 5.0Hz) |
| | | 7.80 (2H, m) |
| | | 8.34 (1H, d, t, 8.1Hz, 2.1Hz) |
| | | 8.89 (1H, d, d, 5.0Hz, 2.1Hz) |
| | | 9.17 (1H, d, 2.1Hz) |

Field desorption mass spectrometry
m/e = 384 (M + 1)$^+$

EXAMPLE II 1.08 g of 2,4-dihydroxy-N-[2-((2-mercaptoethyl) carbamoyl)-ethyl]-3,3-dimethylbutyramide S-nicotinate prepared in the manner described in Example 1 was dissolved in 15 ml of pyridine. Then, 0.75 g of nicotinic acid chloride hydrochloride was added to the solution and heated at 45°–50° C. for 2 hours with stirring. After cooling the reaction solution, precipitated material was removed by filtration. The obtained filtrate was added to 50 ml of 5% sodium bicarbonate solution and extracted with ethylacetate. The extract solution was washed with water, dried and the solvent was evaporated to give a residue containing the desired compound. The residue was placed on a silica gel chromatographic column and elution was carried out with a developing solvent of chloroform-methanol (12:1) to give 0.46 g of 2,4-dihydroxy-N-[2-((2-mercaptoethyl) carbamoyl) ethyl]-3,3-dimethylbutyramide 4, S-dinicotinate as a colorless oily product.

Elemental Analysis $C_{23}H_{28}N_4O_6S$: Calculated: C 56.54, H 5.78, N 11.47, S 6.56: Found: C.56.77, H 5.89, N 11.63, S 6.41.

IR spectra (Liquid-film method) ... FIG. V
NMR spectra

| CD$_3$COCD$_3$ | | |
|---|---|---|
| TMS | δ: | 1.10 (3H, s), 1.15 (3H, s) |
| | | 2.50 (2H, t, 6.7Hz) |
| | | 3.50 (6H, m) |
| | | 4.14 (1H, s) |
| | | 4.33 (2H, s) |
| | | 5.40 (1H, broad) |
| | | 7.70 (4H, m) |
| | | 8.35 (2H, m) |
| | | 8.85 (2H, m) |
| | | 9.13 (1H, d, 2.2Hz), 9.22 (1H, d, 2.2Hz) |

Field desorption mass spectrometry
m/e = 489 (M + 1)$^+$

EXAMPLE III

To a solution of 2.90 g of pantetheine and 60 ml of pyridine, there was added 8.40 g of nicotinic acid chloride hydrochloride. The solution was heated at 45°–50° C. for 2-3 hours with stirring. After the reaction mixture was cooled, a crystalline precipitate was removed by filtration and the filtrate was poured into 300 ml of 5% sodium bicarbonate solution. Then, the solution was extracted with ethylacetate. The obtained extract solution was washed with water, dried and the solvent was evaporated to give a residue. The residue was placed on a silica gel chromatographic column containing 200 g of silica gel and elution was carried out with a developing solvent of chloroform-methanol (15:1) to give 5.05 g of 2,4-dihydroxy-N-[2-((2-mercaptoethyl) carbamoyl)-ethyl]-3,3-dimethoxybutyramide 2,4-S-trinicotinate as colorless powder.

Elemental Analysis $C_{29}H_{31}N_5O_7S$: Calculated: C 58.67, H 5.26, N 11.80, S 5.40: Found: C 58.24, H 5.17, N 11.47, S 5.18.

IR spectra (KBr Tablet method) ... FIG. VI
NMR spectra

| CDCl$_3$ | | |
|---|---|---|
| TMS | δ: | 1.30 (6H, s) |
| | | 2.44 (2H, t, 6.0Hz) |
| | | 3.40 (6H, m) |
| | | 4.39 (2H, s) |
| | | 5.37 (1H, s) |
| | | 7.00 (1H, m) |
| | | 7.30-7.75 (1H, broad) |

-continued

| |
|---|
| 7.46 (3H, d, d, 8.1Hz, 5.2Hz) |
| 8.30 (3H, m) |
| 8.86 (3H, m) |
| 9.20 (1H, d, 2.2Hz), 9.40 (1H, d, 2.2Hz) |
| 9.47 (1H, d, 2.2Hz) |

Field desorption mass spectrometry m/e = 594 (M + 1)$^+$

Having now fully described this invention, it will be apparent to one of ordinary skill in the art that many changes and modifications can be made thereto without departing from the spirit or scope of the invention as set forth herein.

What is claimed as new and intended to be secured by Letters Patent is:

1. A compound of the formula:

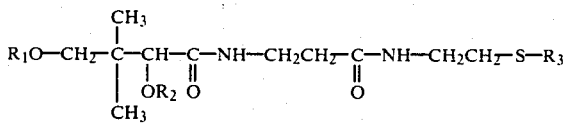

wherein $R_1$, $R_2$ and $R_3$ each represents a member selected from the group consisting of hydrogen and nicotinoyl, with the proviso that $R_1$, $R_2$ and $R_3$ do not all simultaneously represent hydrogen, and the nontoxic acid addition salts thereof.

2. The compound of claim 1, wherein $R_1$ and $R_2$ are hydrogen and $R_3$ is nicotinoyl.
3. The compound of claim 1, wherein $R_1$ is hydrogen and $R_2$ and $R_3$ are nicotinoyl.
4. The compound of claim 1, wherein $R_1$, $R_2$ and $R_3$ are each nicotinoyl.
5. A method of prolonging effective levels of free nicotinic acid in the blood comprising:
   administering to a host subject a therapeutically effective amount of the compound of claim 1.
6. A therapeutic composition, comprising:
   the compound of claim 1 in a pharmaceutically acceptable excipient.

* * * * *